United States Patent [19]

Ogawa et al.

[11] 3,959,375
[45] May 25, 1976

[54] 2,5-DIDEOXYSTREPTAMINE AND THE PRODUCTION THEREOF

[75] Inventors: Seiichiro Ogawa, Hoya; Tetsuo Suami, Musashino, both of Japan

[73] Assignee: Tetsyi Syanu, Musashino, Japan

[22] Filed: Oct. 15, 1974

[21] Appl. No.: 515,094

[52] U.S. Cl.......................... 260/563 R; 260/563 D; 260/309; 195/80 R
[51] Int. Cl.[2].......................................... C07B 91/14
[58] Field of Search.......... 260/563 R, 563 D, 210 S

[56] References Cited
OTHER PUBLICATIONS

Chem. Abs. 11157t 2–Deoxystreptamine Vol. 66, 1967 M. Nakajima.

J. Am. Chem. Soc. Vol. 74, 6/1952, pp. 3187, 3188, The Identity of Neamine & Neomycin A, Leach et al.

J. Am. Chem. Soc. Vol. 73, 2/1951, pp. 881, 882, Kuehl et al., "Streptomyces Antibiotics."

*Primary Examiner*—Allen B. Curtis
*Attorney, Agent, or Firm*—Mason, Fenwick & Lawrence

[57] ABSTRACT

2,5-Dideoxystreptamine is provided which is a new compound useful in the fermentative production of 5-deoxyneamine having useful antibacterial activity by culturing a microorganism. The production of 2,5-dideoxystreptamine is made by catalytic hydrogenation of 6,7-diaza-bicyclo[3.2.1]octane-2,4-diol which is also a new compound.

6 Claims, No Drawings

2,5-DIDEOXYSTREPTAMINE AND THE PRODUCTION THEREOF

This invention relates to 2,5-dideoxystreptamine which is a new compound useful for the fermentative production of an antibacterial substance 5-deoxyneamine which is also a new compound. This invention further relates to a process for the production of 2,5-dideoxystreptamine.

We have now found that a catalytic hydrogenation of 6,7-diaza-bicyclo[3.2.1]octane-2,4-diol with hydrogen gives 2,5-dideoxystreptamine which is a new compound, and that this new compound is useful in that an antibacterial substance, 5-deoxyneamine is produced by culturing a microorganism Streptomyces ribosidificus AF-1 (F.R.I. No. 2131) in a culture medium comprising known carbon source and known nitrogen source in the additional presence of 2,5-dideoxystreptamine, whereas said microorganism does not produce the 5-deoxyneamine in the absence of 2,5-dideoxystreptamine. It is expected that 2,5-dideoxystreptamine may also be used as an intermediate in the production of semi-synthetic other antibiotics.

As the 2,5-dideoxystreptamine is a basic substance, it forms an acid-addition salt with a mineral acid such as hydrochloric acid, nitric acid, sulfuric acid, phosphoric acid and the like or with an organic acid such as acetic acid, propionic acid, citric acid, tartaric acid and the like.

According to this invention, therefore, there is provided 2,5-dideoxystreptamine of the formula

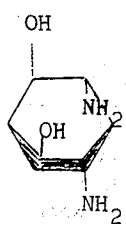

and an acid-addition salt thereof.

2,5-Dideoxystreptamine (the free base) has a melting point of 198°C.

2,5-Dideoxystreptamine dihydrochloride is in the form of colorless platelets of a melting point of 290°–295°C and is soluble in water and methanol or ethanol. This substance is little toxic ($LD_{50}$:> 1 g/kg upon intraperitoneal injection in mice).

According to this invention, there is further provided a process for the production of 2,5-dideoxystreptamine, which comprises hydrogenating 6,7-diaza-bicyclo[3.2.1]octane-2,4-diol with hydrogen in the presence of a known hydrogenation catalyst.

The 6,7-diaza-bicyclo[3.2.1]octane-2,4-diol which is employed as the starting material in the process of this invention is represented by the formula

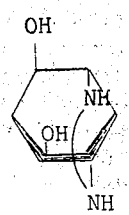

and may be prepared by epoxidizing 1,4-cyclohexadiene in a known manner, for example, by reacting with a peroxide such as benzoyl peroxide and the like and then reacting the resulting cis-1,4-di-epoxycyclohexane with hydrazine in a solvent such as 2-methoxyethanol.

In carrying out the process of this invention, the starting 6,7-diaza-bicyclo[3.2.1]octane-2,4-diol may preferably be dissolved in water or an inert organic solvent such as methanol, ethanol or other solvent, and the solution is subjected to the hydrogenation in the presence of a known hydrogenation catalyst such as Raney nickel, a platinum group metal, particularly platinum, palladium, palladium-on-carbon, rhodium and the like. Of course, the platinum group metal may be used in the form of their oxides or as the mixtures of them. The hydrogenation may be conducted under atmospheric pressure, that is, at about 1 kg/cm², but it is convenient that the hydrogenation is effected under a super-atmospheric pressure of up to 50 kg/cm² in order to reduce the required reaction time. The reaction temperature may conveniently be in a range of ambient temperature to 150°C, and the reaction time may suitably be in a range of 1 to 24 hours. After the reaction has been completed, the reaction mixture may be filtered to remove the catalyst, and the filtrate may be concentrated under a reduced pressure to recover the desired 2,5-dideoxystreptamine as a crystalline residue. A crude 2,5-dideoxystreptamine may be purified by recrystallization from its aqueous solution.

This invention is now illustrated with reference to the following Examples to which this invention is not limited.

EXAMPLE 1

Preparation of 6,7-diaza-bicyclo[3.2.1]octane-2,4-diol 0.59 Grams of cis-1,4-di-epoxycyclohexane (prepared from 1,4-cyclohexadiene by the method of T.W. Graig, G.R. Harvey & G.A. Berchtold described in the "Journal of Organic Chemistry" Vol. 32, 3745 (1967)) were admixed with 55 ml of 2-methoxyethanol and 1.4 ml. of anhydrous hydrazine, and the resulting admixture was heated for 5 hours under reflux. The reaction mixture was allowed to cool and then distilled under a reduced pressure to remove the solvent (2-methoxyethanol) and the excess reagents. The crystalline residue obtained was triturated together with ethanol and allowed to stand. The solid was removed by filtration, washed with ethanol and then dried under a reduced pressure, affording 0.58 g of 6,7-diaza-bicyclo[3.2.1]octane-2,4-diol. Yield 77%. m.p. 203°–205°C.

Elemental analysis: Calculated for $C_6H_{12}N_2O_2$: C, 49.98; H, 8.39; N, 19.43%. Found: C, 50.49; H, 7.83; N, 18.93%.

When this substance was left in the air, it became moistened and discolored into brown.

EXAMPLE 2

Production of 2,5-dideoxystreptamine 6,7-Diaza-bicyclo[3.2.1]octane-2,4-diol (0.20 g) was dissolved in 20 ml. of a mixture of water and ethanol (1:1 by volume) to which was then added 0.2 g of Ranney nickel. The admixture was shaken for 15 hours under an atmosphere of hydrogen at a pressure of 3.4 kg/cm² for the hydrogenation. The reaction mixture was filtered to remove the catalyst, and the filtrate was concentrated under reduced pressure, giving a crystalline residue. This solid was dispersed in ethanol, removed by filtraton and then dried to afford 0.18 g of 2,5-dideoxystreptamine. Yield 91%. mp. 198°C. This substance was taken up into water, and to the resulting aqueous solution was added a slight excess of 1N hydrochloric acid. The mixture was concentrated by evaporation of the solvent, giving colorless platelets. Recrystallization of this product from water-ethanol gave 2,5-dideoxystreptamine dihydrochloride as colorless platelets of mp. 290°–295°C.

Elemental analysis: Calculated for $C_6H_{14}N_2O_2 \cdot 2HCl$: C, 32.89; H, 7.36, N, 12.79; Cl, 32.36%. Found: C, 32.76; H, 7.15; N, 12.41; Cl 32.04%.

EXAMPLE 3

Production of N,N'-diacetyl-2,5-dideoxystreptamine

A solution of 40 mg of 2,5-dideoxystreptamine (the free base) in 5 ml. of methanol was admixed with 1 ml. of acetic anhydride, and the admixture was allowed to stand overnight to deposit crystals. The crystals were collected by filtration, washed with methanol and then dried over anhydrous calcium chloride. Yield 38 mg. The product was identified as N,N'-diacetyl-2,5-dideoxystreptamine hydrate and showed a melting point of 297°–301°C.

Elemental analysis: Calculated for $C_{10}H_{18}N_2O_4$: C, 52.16; H, 7.88; N, 12.17%. Found: C, 52.01; H, 7.64; N, 12.02%.

When 2,5-dideoxystreptamine was treated with acetic anhydride and pyridine in a similar way, there was formed tetra-N,O-acetyl-2,5-dideoxystreptamine.

EXAMPLE 4

Production of 5-deoxyneamine

This example shows a utility of 2,5-dideoxystreptamine. A sterile culture medium comprising 5% starch, 3% soybean meal, 0.8% sodium nitrate, 0.01% calcium carbonate and 0.005% ferric sulfate was prepared and 80 ml. of this culture medium was placed in each Sakaguchi flask, adjusted to pH 7.5 and then inoculated with Streptomyces ribosidificus AF-1 (F.R.I. No. 2131, this strain was deposited in the "Fermentation Research Institute", Agency of Industrial Science and Technology, Inage, Chiba City, Japan). The flasks were incubated at 28°–31°C under aeration.

After 24 hours incubation, 2,5-dideoxystreptamine was admixed at a concentration of 436 mcg/ml. with the incubated culture medium in each flask, and the incubation was further carried out for 5 days. The cultures so obtained were combined together and filtered. The resulting culture broth filtrate was passed through a column of 10 ml. of a cation-exchange resin Amberlite IRC-50 (a product of Rhom & Haas Co., U.S.A.) ($Na^+$ type) for the adsorption. The column was then washed with 100 ml. of water and then eluted with 1N aqueous ammonia. The eluate was collected, concentrated under reduced pressure and then freeze-dired, giving 67 mg of a crude powder.

This powder was taken up into a small volume of water and the aqueous solution was adjusted to pH 7 by addition of hydrochloric acid and then passed through a column of 10 ml. of a cation-exchange resin Amberlite CG-50 (a product of Rhom & Haas Co., U.S.A.) ($Na_4^+$ type) for adsorption. The column was then washed with 200 ml. of water and then with 100 ml. of 0.1 N aqueous ammonia and subsequently gradient-eluted with 0.0 N to 0.3N aqueous ammonia. The eluate was collected in 10 ml. fractions, and such active fractions which gave a single spot in the vicinity of $Rf_{neamine} = 0.88$ in a silica gel thin layer chromatography (developed with a mixed solvent of 1:4:2:1 chloroform-methanol-ammonia-water) were combined together. The combined solution was concentrated by evaporation of the solvent under reduced pressure and then freezedried, affording 14 mg of a powder. This pulver substance was identified as 5-deoxyneamine by a gas-liquid chromatography and mass spectrometery. This powder substance, 5-deoxyneamine showed the following antibacterial spectrum when it was estimated in an agar medium incubated at 37°C for 18 hours.

TABLE 1

| Antibacterial spectrum of 5-deoxyneamine | |
|---|---|
| Test Microorganism | Minimum Inhibitory Concentration (mcg/ml.) |
| Staphylococcus aureus 209P | 3.12 |
| Escherichia coli NIHJ | 6.25 |
| "   K-12 CS-2 | 6.25 |
| "   K-12 ML1629 | >100 |
| "   K-12 ML1630 | >100 |
| "   K-12 ML1410 | 6.25 |
| Salmonella typhosa | 3.12 |
| Pseudomonas aeruginosa | >100 |
| Proteus rettgeri GN 311 | 25 |
| "   GN 466 | 12.5 |

When the above-mentioned procedure of incubating the microorganism Streptomyces ribosidificus AF-1 was repeated in the same culture medium but without the addition of 2,5-dideoxystreptamine, the 5-deoxyneamine could not be recovered from the culture medium which had been incubated for 7 days, indicating that the presence of 2,5-dideoxystreptamine in the culture medium contributed to the production of 5-deoxyneamine by said strain.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of this invention to adapt it to various usage conditions.

What we claim is:

1. 2,5-Dideoxystreptamine of the formula

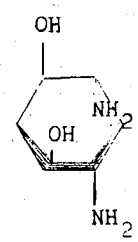

and an acid-addition salt thereof.

2. A compound as claimed in claim 1, which is 2,5-dideoxystreptamine dihydrochloride.

3. A process for the production of 2,5-dideoxystreptamine as claimed in claim 1, which comprises hydrogenating 6,7-diaza-bicyclo[3.2.1]octane-2,4-diol with hydrogen in the presence of a known hydrogenation catalyst.

4. A process as claimed in claim 3 in which 6,7-diazabicyclo[3.2.1]octane-2,4-diol is hydrogenated in solution in water or in methanol or ethanol.

5. A process as claimed in claim 3 in which the hydrogenation is carried out at a temperature of from ambient temperature to 150°C for a reaction time of from 1 to 24 hours under a pressure of 1 to 50 kg/cm$^2$.

6. A process as claimed in claim 3 in which the hydrogenation catalyst is Raney nickel, platinum, palladium or palladium-on-carbon.

* * * * *

Notice of Adverse Decision in Interference

In Interference No. 99,533, involving Patent No. 3,959,375, S. Ogawa and T. Suami, 2,5-DIDEOXYSTREPTAMINE AND THE PRODUCTION THEREOF, final judgment adverse to the patentees was rendered Aug. 29, 1977, as to claims 1–4 and 6.

[*Official Gazette December 20, 1977.*]